United States Patent [19]
Kert

[11] Patent Number: 6,010,335
[45] Date of Patent: Jan. 4, 2000

[54] ENDODONTIC DEVICE FOR APPLYING A FILLER MATERIAL TO A ROOT CANAL OF A TOOTH

[76] Inventor: Jimmie Kert, Wildersgade 55, DK-1408, Copenhagen K, Denmark

[21] Appl. No.: 09/229,310

[22] Filed: Jan. 13, 1999

[51] Int. Cl.[7] .................................................. A61C 5/02
[52] U.S. Cl. ............................................. 433/81; 433/224
[58] Field of Search .............................. 433/81, 102, 224

[56] References Cited

U.S. PATENT DOCUMENTS

| 4,332,561 | 6/1982 | McSpadden | 433/102 |
| 5,118,297 | 6/1992 | Johnson | 433/81 |
| 5,648,403 | 7/1997 | Martin | 433/228.1 |
| 5,882,196 | 3/1999 | Kert | 433/81 |

FOREIGN PATENT DOCUMENTS

96/12445  5/1996  WIPO .

*Primary Examiner*—John J. Wilson
*Attorney, Agent, or Firm*—Larson & Taylor

[57] ABSTRACT

A dental device for applying a thermoplastic filler material comprising thermoplastic gutta percha to a root canal of a tooth. The device comprises an elongated shaft of flexible material having a distal end forming a core for a layer of thermoplastic filler material surrounding at the least distal end said shaft. The layer of filler material comprises an anti-microbiological substance for preventing or at least reducing the risk of irritation, inflammation or infection.

7 Claims, 1 Drawing Sheet

ENDODONTIC DEVICE FOR APPLYING A FILLER MATERIAL TO A ROOT CANAL OF A TOOTH

TECHNICAL FIELD

The present invention relates to dental devices for applying a filler material to a root canal used in filling an endodontically prepared root canal or the like.

BACKGROUND ART

WO 96/12445 describes a device, also referred to as obturator, for applying filler material, such as gutta percha or the like, to an endodontically prepared root canal or a tooth of a patient The device which Is disclosed in this patent generally comprises a core member, or tool, in the form of an elongated shaft of flexible material having a distal end portion and a proximal end portion. The distal end portion is covered with a sleeve of thermoplastic material. The sleeve is heated up before the obturator is inserted into the root canal. Thus, the thermoplastic sleeve becomes plastic and the thermoplastic sleeve will easily adapt to the anatomy of the root canal. However, due to irregularities in the shape of the canals or incomplete preparation of the canal, the thermoplastic sleeve does not always completely seal off all parts of the canal. A not completely sealed root canal can lead to irritations of the affected area or bacterial contamination leading to infection and failure of the root canal. Even when the thermoplastic material does seal the opening of the canal completely or almost completely, a gradual leaching out process from contact with tissue fluid will create more voids and poorer adaptation within the canal anatomy. These processes can lead to irritations, inflammations, and/or infected root canals which cause the patient discomfort and pain or even loss of the tooth.

Although the obturator with its sleeve of thermoplastic filler material has been a great step forward in improving the chances of completely filling a root canal, there still remains a small risk that a small part of the canal is not completely filled. Such small cavities can due to contact with tissue fluids create discomfort and pain to the patient.

DISCLOSURE OF THE INVENTION

It is the object of the present invention to provide a dental device for applying filler material to a root canal of a tooth which reduces the risk of inflammation or infection, also when the canal is not completely and perfectly filled. This object is achieved with a dental device which is of a nature discussed in more detail below. This device allows a near perfect filling of the root canal. The thermoplastic layer is heated to a degree in which the filler material is plastic, whereafter the plastic material, supported by the elongated shaft of flexible material, is inserted into the root canal, thereby filling also irregular shapes due to the plasticity of the filler material. If the filling was, however, not perfect due to serious irregularities of the canal, incomplete preparation of the root canal or due to leaching out of the filler material under influence of tissue liquid over the lifetime of the filling, which can be required to be more than 60 years, the provision of an anti-microbiological agent in the sleeve of thermoplastic material will prevent or at least reduce the risk of irritation, inflammation and infection.

The layer of filler material bases its thermoplastic effect on the presence of thermoplastic gutta percha. Gutta percha in its natural form, the so-called beta-phase is thermosetting, and therefore not suited for use with the present invention. The recently developed thermoplastic form, also referred to as the alpha-phase, which is achieved by a new milling process, renders the gutta percha thermoplastic.

According to another embodiment of the invention, the thermoplastic layer further comprises substances such as iron sulphate, zinc oxide, titanium oxide, wax and colour and antioxidants.

According to a further embodiment, the device is provided with a releasable handle.

BRIEF DESCRIPTION OF THE DRAWINGS

In the following detailed portion of the present description, the invention will be explained in more detail with reference to the embodiments of the device according to the invention diagrammatically shown in the drawings, in which.

DESCRIPTION OF THE PREFERRED EMBODIMENT

Figure 1:
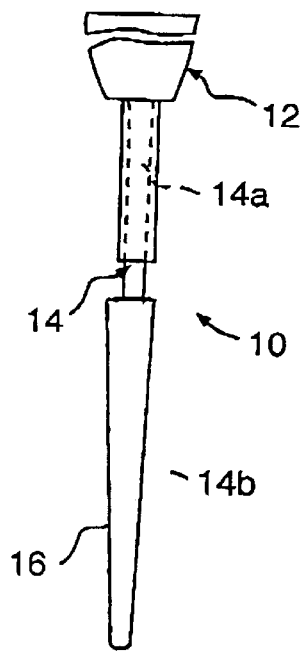
FIG. 1 shows a first embodiment of the obturator according to the invention.

The endodontic obturator shown in the drawings comprises an elongated shaft 14 of flexible material, e.g. suitable plastic material, having a distal end portion 14b forming a core for a layer of thermoplastic filler material 16 surrounding at least said distal end 14b of said shaft 14.

Figure 2:
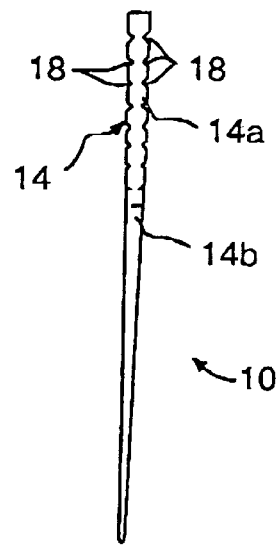
FIG. 2 shows the flexible shaft as such for use with the first embodiment of the invention.
Figure 3:
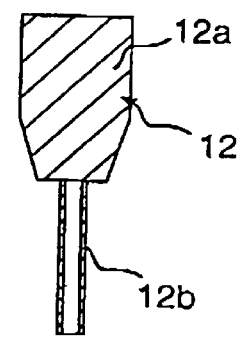
FIG. 3 shows a handle device as such for use with the first embodiment.

The elongated shaft 14 of flexible material has a proximal end portion 14a at the opposite side of the tapered distal portion 14b. A handle device 12, 22 is attached to the proximate end of the elongated shaft 1. The handle device 12, 22 includes a portion 12a, 22a for gripping by a user. According to a preferred embodiment, the handle is integral with the flexible shaft (not shown). The handle device 12, 22 may according to other embodiments be attached releasably to the shaft. For the releasable attachment, the handle device may according to one embodiment as shown in FIGS. 1–3 include a hollow tubular member 12b extending outwardly therefrom which, as Shown in FIG. 2, fits around the proximal end portion 14a of the elongated shaft 14.

Figure 4:
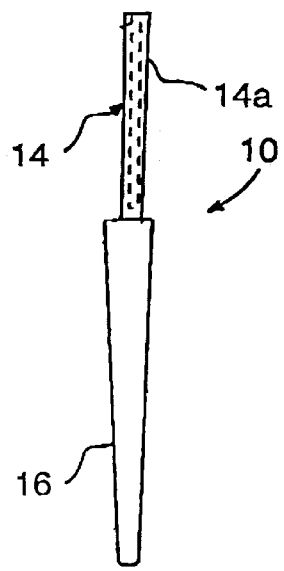
FIG. 4 shows a second embodiment according to the invention.
Figure 5:
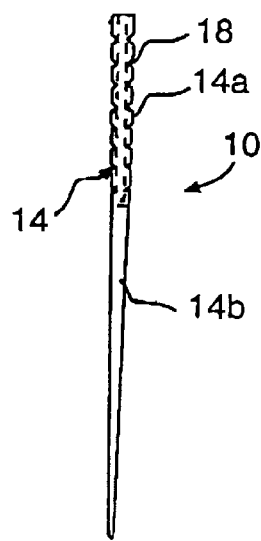
FIG. 5 shows the flexible shaft as such for use with the second embodiment of the invention.
Figure 6:
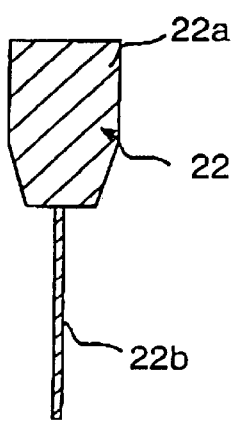
FIG. 6 shows a handle device as such for use with the second embodiment.

According to another embodiment, as shown in FIGS. 4–6, an axial or longitudinal bore is provided in the proximal end portion 14a.

The bore is used to permit gripping of the flexible shaft 14 by a handle device 22 as shown in FIG. 6.

The handle device 22 as shown in FIG. 6 Includes a handle portion 22a and a solid shank 22b which extends outwardly therefrom.

A tapered or conically shaped layer of thermoplastic material 16 comprising thermoplastic gutta percha surrounds the tapered distal portion 14b of the elongated shaft 14.

As shown in FIGS. 2 and 5, the proximal end portion 14b of the elongated shaft 14 may be provided with a plurality of longitudinally spaced grooves 18, which form a scale or indicator means. More particularly, grooves 18 provide a user with an indication of the length of the elongated shaft 14 at various points therealong and thus assist the user in cutting off the elongated shaft 14 at the point which produces an elongated shaft 14 of the desired length, based on the length of the root canal to be filled.

The elongated shaft 14 is according to a preferred embodiment made of a biocompatible material such as thermoplastic polymer or a mixture of thermoplastic polymers.

When the root canal has been prepared, the dental device is inserted in the canal with the cone-shaped layer of thermoplastic material 16 leading, after suitable preheating to make it sufficiently soft to adapt itself to the walls of the root canal. During the insertion, the device is held and moved by means of the handle 12, 22.

When the device has been placed in its final position in the root canal, and sufficient time has elapsed to allow it to set, the handle 12, 22 is removed. When the handle 12, 22 has been removed, any excess shaft material may be removed, after which the root canal is closed and provided with a top filling in a conventional manner.

The layer of thermoplastic material is according to a preferred embodiment of the invention made of a composition of (weight %)

25% alpha-phase gutta percha,
25% barium sulphate,
24% zinc oxide,
10% titanium dioxide,
10% iodine,
5% wax, and
1% colour and antioxidant.

Variations to the above composition can be made by up to 15% without loosing the desired properties. The anti-microbiological substance has an active component selected from the group consisting of compounds of iodine, fluor and combinations thereof. The compounds are chosen such that when the thermoplastic layer is breaking down due to tissue secretions the compound is dissolved into its elements and thereby the ions of the mentioned group of substances will become active.

The form of iodine to be used in the present invention is substantially pure iodine. This form is easily mixed into the thermoplastic material as defined above and is inactive unless it dissolves in tissue fluid. The obturator will then release its iodine. The amount of iodine used in the thermoplastic material is 5–10 weight %.

According to another embodiment of the present invention, the active component is fluor. The form of fluor to be used in the present invention is fluorite. This form is already widely used in endodontal practice for the fluoridation of teeth. It, therefore, combines the merits of an anti-microbiological agent together with a fluoridation of the inner walls of the root canal, thereby reinforcing the crystal matrix of the tooth material. Fluorite will by gradual release both reduce the risk of inflammation and infection and will prevent the inner walls of the root canal from decay. The amount of fluorite used in the thermoplastic material is 1–5 weight %.

The layer of thermoplastic material is for the embodiment using fluorite preferably made of a composition of (weight %)

27% alpha-phase gutta percha,
26% barium sulphate,
26% zinc oxide,
10% titanium dioxide,
5% fluorite,
5% wax, and
1% colour and antioxidant.

Combinations of the before-mentioned anti-microbiological substance can be used according to circumstances.

The new composition of the thermoplastic layer of filler material will allow a further step in ensuring successful obturation of root canals and reduce substantially the risk of inflammation and infection. The dental device according to the invention will therefore offer a further improvement against unsuccessful root canal obturation. It is understood that the above description is illustrated only, and variations in the concentration of the substances can be made.

LIST OF PARTS 10 obturator
12 handle
12a portion for gripping
12b hollow tubular member
14 elongated flexible shaft
14a proximate end portion
14b distal end portion
16 layer of thermoplastic material
18 groove

I claim:

1. A dental device for applying a filler material to a root canal of a tooth comprising:

an elongated shaft of flexible material having a distal end portion forming a core, and a layer of thermoplastic filler material surrounding at least said distal end of said shaft, the layer of filler material comprising in weight %:
21.25–28.75% alpha-phase gutta percha,
21.25–28.75% barium sulphate,
20.40–27.60% zinc oxide,
8.50–11.50% titanium dioxide,
5.00–10.00% iodine,
4.25–5.75% wax, and
8.85–1.15% color and antioxidant.

2. A dental device according to claim 1, wherein the elongated shaft of flexible material has a proximal head portion (3) which is not covered by the layer of thermoplastic material.

3. A dental device according to claim 2, wherein a handle is releasably affixed to said proximal end.

4. A dental device according to claim 2, characterised by the shaft being made from a biocompatible polymer.

5. A dental device according to claim 1, characterised in that the thermoplastic filler material is composed in weight %:

25% thermoplastic gutta percha,
25% barium sulfate,
25% zinc oxide,
9% titanium dioxide,
5% wax,
1% color and antioxidant, and
10%.

6. A dental device for applying a filler material to a root canal of a tooth comprising:

an elongated shaft of flexible material having a distal end portion forming a core, and a layer of thermoplastic filler material surrounding at least said distal end of said shaft, the layer of filler material comprising thermoplastic gutta percha and an antimicrobiological substance with an active component comprising 1–5 weight % fluorite.

7. A dental device for applying a filler material to a root canal of a tooth comprising:

an elongated shaft of flexible material having a distal end portion forming a core, and a layer of thermoplastic filler material surrounding at least said distal end of said shaft, the layer of filler material comprising in weight %:

27% alpha-phase gutta percha,

26% barium sulphate,

26% zinc oxide,

10% titanium dioxide,

5% fluorite,

5% wax, and

1% color and antioxidant.

* * * * *